(12) United States Patent
Harvey et al.

(10) Patent No.: US 10,106,475 B1
(45) Date of Patent: Oct. 23, 2018

(54) HIGH DENSITY TURBINE AND DIESEL FUELS FROM TRICYCLIC SESQUITERPENES

(71) Applicant: The United States of America as Represented by the Secretary of the Navy, Washington, DC (US)

(72) Inventors: Benjamin G. Harvey, Ridgecrest, CA (US); Kale Warren Harrison, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/680,909

(22) Filed: Aug. 18, 2017

Related U.S. Application Data

(63) Continuation-in-part of application No. 14/311,588, filed on Jun. 23, 2014, now Pat. No. 9,546,332, which is a continuation-in-part of application No. 15/099,190, filed on Apr. 14, 2016, now Pat. No. 9,738,843, and a continuation-in-part of application
(Continued)

(51) Int. Cl.
| | |
|---|---|
| *D03D 23/00* | (2006.01) |
| *C07C 5/03* | (2006.01) |
| *C07C 5/31* | (2006.01) |
| *C07C 4/06* | (2006.01) |
| *C10L 1/08* | (2006.01) |
| *C10L 10/12* | (2006.01) |
| *C06B 43/00* | (2006.01) |
| *D03D 43/00* | (2006.01) |

(52) U.S. Cl.
CPC .............. *C07C 5/03* (2013.01); *C06B 43/00* (2013.01); *C07C 4/06* (2013.01); *C07C 5/31* (2013.01); *C10L 1/08* (2013.01); *C10L 10/12* (2013.01); *C07C 2527/126* (2013.01); *C07C 2603/74* (2017.05); *C10L 2200/0469* (2013.01); *C10L 2270/026* (2013.01)

(58) Field of Classification Search
USPC .......................................... 149/109.6, 109.4
See application file for complete search history.

(56) References Cited

U.S. PATENT DOCUMENTS

| | | | |
|---|---|---|---|
| 5,858,766 A | 1/1999 | Premuzic | |
| 9,777,234 B1 * | 10/2017 | Harvey | ................... C06B 47/00 |
| 2015/0011810 A1 | 1/2015 | Harvey | |

OTHER PUBLICATIONS

Chung, et al. Recent developments in high-energy density liquid hydrocarbon fuels, Energy & Fuels, 1999, 13, 641-649.
(Continued)

*Primary Examiner* — James E McDonough
(74) *Attorney, Agent, or Firm* — Charlene A. Haley

(57) ABSTRACT

A method for converting cedarwood oil into high density fuels including, hydrogenating cedarwood oil in the presence of at least one hydrogenation catalyst to generate hydrogenated cedarwood oil, removing the hydrogenation catalyst from the hydrogenated cedarwood oil, purifying the hydrogenated cedarwood oil to produce a first high density fuel, isomerizing the first high density fuel in the presence of at least one acid catalyst to generate a hydrocarbon mixture including adamantanes, and distilling the adamantane mixture to produce a second alkyl-adamantane high density fuel.

1 Claim, 10 Drawing Sheets cedrol      α-cedrene      cedrane      ETMA

Related U.S. Application Data

No. 15/297,285, filed on Oct. 19, 2016, now Pat. No. 9,758,737.

(60) Provisional application No. 61/840,004, filed on Jun. 27, 2013.

(56) References Cited

OTHER PUBLICATIONS

Ma, et al. Ionic liquids catalytic rearrangment of polycyclic hydrocarbos: a versatile route to alkyl-diamondoid fuels, Amer. Chem. Soc. 2013, 2486-2492.

Badme, et al. Generation of C11-C17 monoalkyladamantane via catalysis of some-O2_containing precursors of Pet. Hydrocarbons. Petroleum Chemisrty 2011, 51, 331-335.

* cited by examiner

HIGH DENSITY TURBINE AND DIESEL FUELS FROM TRICYCLIC SESQUITERPENES

CROSS-REFERENCE TO RELATED APPLICATIONS

This is a divisional patent application of Ser. No. 15/371,301 filed on Dec. 7, 2016, which claims benefit of and is a continuation-in-part patent application, claiming benefit of, parent patent application Ser. No. 14/311,588 filed on Jun. 23, 2014, which is the parent patent application, claiming the benefit of, parent provisional patent application Ser. No. 61/840,004 filed on Jun. 27, 2013, and is a continuation-in-part of patent application Ser. No. 15/099,190 filed on Apr. 14, 2016 and is a continuation-in-part of patent application Ser. No. 15/297,285 filed on Oct. 19, 2016, whereby the entire disclosures of which are incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to methods to convert cedar wood oil and/or components of cedar wood oil that can be prepared via biosynthetic routes to high density fuels including alkyl diamondoids.

Figure 1:
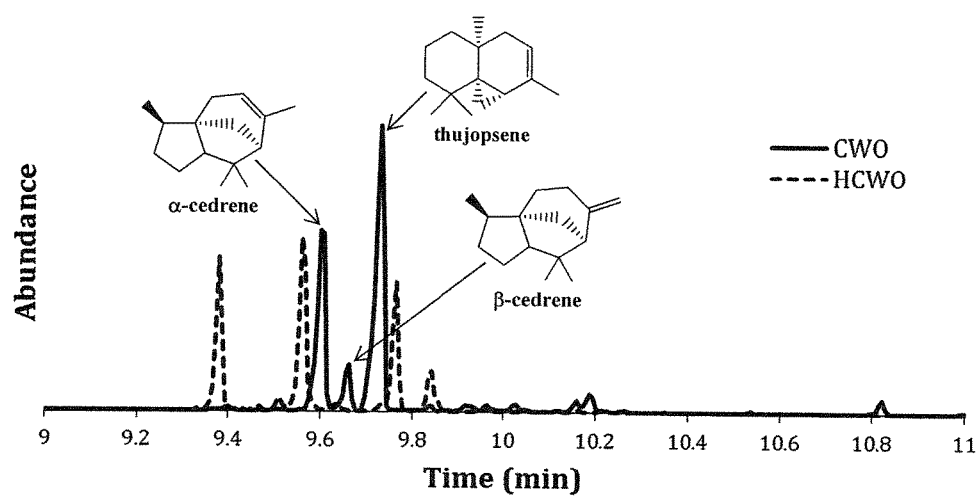
FIG. 1 is a GC chromatogram of Cedarwood oil (CWO) and hydrogenated Cedarwood oil (HCWO), according to embodiments of the invention.

It is to be understood that the following detailed descriptions are exemplary and explanatory only and are not to be viewed as being restrictive of the invention, as claimed.

Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

Embodiments of the invention include at least three new advanced biofuels have been produced from sesquiterpene feedstocks. Cedarwood oil, which is primarily composed of the sesquiterpenes thujopsene, α-cedrene, and β-cedrene, was hydrogenated to generate a fuel blend (HCWO) with a cetane number of 31 and a volumetric net heat of combustion (NHOC) more than 12% higher than conventional jet fuel. Hydrogenation under pressures between 30 and 5000 psi allowed for reduction of the double bond in thujopsene while keeping the cyclopropane ring intact. A single component high density fuel containing only hydrogenated α-cedrene (cedrane) was then prepared from α-cedrol and found to have an even higher NHOC and lower viscosity than HCWO. Cedrane was then isomerized to 1-ethyl-3,5,7-trimethyladamantane (ETMA) and a mixture of other alkyl adamantanes. The adamantane mixture had a remarkable cetane number of 46 and a viscosity suitable for use in a conventional diesel engine. This work shows that sustainable multicyclic sesquiterpenes are versatile feedstocks to ultra-performance fuels that combine both high densities and high cetane numbers.

Recent oil discoveries around the globe, improved technology to utilize non-traditional oil resources, and the ready availability of cheap natural gas have exerted downward pressure on the price of oil. However, in light of world population growth and the desire by developing economies to mimic the energy intensive growth strategies employed in the past, this trend is clearly unsustainable. For these reasons, development of sustainable alternatives to jet and diesel fuel continues to be an area of active study. (Wei-Cheng, W.; Ling, T. *Ren. Sust. Energy Rev.* 2016, 53, 801-822; Bond, J. Q.; Upadhye, A.; Hakan, O. et al. *Energy Environ. Sci.* 2014, 7, 1500-1523; Harvey, B. G.; Meylemans, H. A. *Green Chem.* 2014, 16, 770-776; Harvey, B. G.; Meylemans, H. A. *J. Chem. Technol. Biotechnol* 2011, 86, 2-9; Harvey, B. G.; Quintana, R. L. *Energy Environ. Sci.* 2010, 3, 352-357; Wright, M. E.; Harvey, B. G.; Quintana, R. L. *Energy Fuels* 2008, 22, 3299-3302)

Research in this area is motivated both by the desire to combat the effects of global warming as well as to provide for the long term needs of vehicles that require energy dense, drop-in fuels. Although 1$^{st}$ generation biofuels suffer from performance issues including low densities, low volumetric net heats of combustion, and inferior compatibility with existing engines, recent work has shown that advanced renewable fuels with higher densities and NHOCs than conventional petroleum-based fuels can be generated from terpenoids. (Harvey, B. G.; Merriman, W. W.; Koontz, T. A. *Energy Fuels* 2015, 29, 2431-2436; Harvey, B. G.; Meylemans, H. A.; Gough, R. V.; Quintana, R. L.; Garrison, M. D.; Bruno, T. *J. Phys. Chem. Phys.* 2014, 16, 9448-9457; Liang, R.; Harvey, G. G.; Quintana, R. L.; Suflita, J. M. *Energy Fuels* 2015, 29, 5164-5170; Meylemans, H. A.; Quintana, R. L.; Rex, M. L.; Harvey, B. G. *J. Chem. Technol. Biotechnol.* 2014, 89, 957-962; Meylemans, H. A.; Baldwin, L. C.; Harvey, B. G. *Energy Fuels* 2013, 27, 883-888; Meylemans, H. A.; Quintana, R. L.; Harvey, B. G. *Fuel* 2012, 97, 560-568; Meylemans, H. A.; Quintana, R. L.; Goldsmith, B.

R.; Harvey, B. G. *ChemSusChem* 2011, 4, 465-469; Harvey, B. G.; Wright, M. E.; Quintana, R. L. *Energy Fuels* 2010, 24, 267-273)

In previous work, our group explored the use of sesquiterpenes as substrates for the generation of high energy density fuels. (Harvey, B. G.; Merriman, W. W.; Koontz, T. A. *Energy Fuels* 2015, 29, 2431-2436: Harvey, B. G.; Meylemans, H. A.; Gough, R. V.; Quintana, R. L.; Garrison, M. D.; Bruno, T. *J. Phys. Chem. Phys.* 2014, 16, 9448-9457) Sesquiterpenes are naturally occurring trimers of isoprene that can be acyclic, bicyclic, tricyclic, and even tetracyclic. This class of hydrocarbons can be isolated from trees and other biomass sources or prepared from biomass sugars with metabolically engineered bacteria or yeast. (George, K. W.; Alonso-Gutierrez, J.; Keasling, J. D.; Lee, T. S. *Adv. Biochem. Engineering/Biotechnology* 2015, 148, 355-89; Buijs, N. A.; Siewers, V.; Nielsen, *J. Curr. Opin. Chem. Biol.* 2013, 17, 480-488; Phelan, R. M.; Sekurova, O. N.; Keasling, J. D.; Zotchev, S. B. *ACS Synth. Biol.* 2015, 4, 393-399; Peralta-Yahya, P. P.; Ouellet, M.; Chan, R.; Mukhopadhyay, A.; Keasling, J. D.; Lee, T. S. *Nat. Comm.* 2011, 1494/1-1494/8)

Researchers are also studying methods to directly produce these molecules in trees and other plants. (Zerbe, P.; Bohlmann, *J. Recent Adv. Phytochem.* 2014, 44, 85-107; Lange, B. M.; Ahkami, A. *Plant Biotech. J.* 2013, 11, 169-196) These advances would potentially allow for generation of sesquiterpenes on a commercial scale. As the volumetric net heat of combustion of a fuel is highly dependent on the density, multicyclic sesquiterpenes are the most useful class of sesquiterpenes for high energy density fuels. (Harvey, B. G.; Merriman, W. W.; Koontz, T. A. *Energy Fuels* 2015, 29, 2431-2436: Harvey, B. G.; Meylemans, H. A.; Gough, R. V.; Quintana, R. L.; Garrison, M. D.; Bruno, T. *J. Phys. Chem. Phys.* 2014, 16, 9448-9457) To generate stable fuels sesquiterpenes can simply be hydrogenated and/or isomerized with heterogeneous acid catalysts to generate unique fuel mixtures. The latter approach allows for modification of the fuel properties including density, viscosity, net heat of combustion, and even cetane number.

Cedarwood oil is an intriguing starting material for advanced biofuel development. It primarily contains the tricyclic sesquiterpenes α-cedrene, β-cedrene, and thujopsene along with a significant quantity of cedrol. Cedarwood oil derived from redcedar has previously been investigated as a fuel product, and epi-cedrol has been generated from glucose with metabolically engineered yeast. (Eller, F. J.; King, J. W. *Phytochem. Anal.* 2000, 11, 226-231; Yang, Z.; Kumar, A.; Huhnke, R. L.; Buser, M.; Capareda, S. *Fuel* 2016, 166, 157-165; Jackson, B. E.; Hart-Wells, E. A.; Matsuda, S. P. T. *Org. Lett.* 2003, 5, 1629-1632) This work suggests that significant quantities of these sesquiterpenes could be generated biosynthetically. Although simple hydrogenation of cedarwood oil could generate a fuel blend, it was also of interest to see if strong Lewis acid catalysts could potentially convert the tricyclic sesquiterpenes into tetracyclic structures with increased densities and NHOC. A number of reports have shown that multicyclic hydrocarbons can be isomerized to tetracyclic alkyl adamantanes by Lewis acid catalyzed isomerization. In some cases these isomerizations are selective for a specific alkyl diamondoid. In a particularly elegant example, Schleyer showed that the hydrogenated sesquiterpene cedrane could be readily isomerized to the tetracyclic hydrocarbon 1-ethyl-3,5,7-trimethyl adamantane in high yield. (Schleyer, P.; Gleicher, G. J.; Cupas, C. A. *J. Org. Chem.* 1966, 31, 2014-2015; Schneider, A.; Warren, R. W.; Janoski, E. J. *J. Org. Chem.* 1966, 31, 1617-1625; Schneider, A.; Warren, R. W.; Janoski, E. J. *J. Am. Chem. Soc.* 1964, 86, 5365-5367; Nomura, M.; Schleyer, P.; Arz, A. *J. Am. Chem. Soc.* 1967, 89, 3657-3659; Engler, E. M.; Farcasiu, M.; Sevin, A.; Cense, J. M.; Schleyer, R. *J. Am. Chem. Soc.* 1973, 95, 5769-5771)

Alkyl adamantanes are an intriguing class of molecules that have been explored as high density fuels for volume-limited aircraft. In a recent paper our group showed that attachment of short alkyl chains to the adamantane core resulted in fuels with outstanding densities, NHOCs, and cetane numbers. (Chung, H. S.; Chen, C. S. H.; Kremer, R. A.; Boulton, J. R. Burdette, G. W. *Energy Fuels* 1999, 13, 641-649; Ma, T.; Feng, R.; Zou, J-J.; Zhang, X.; Wang, L. *Ind. Eng. Chem. Res.* 2013, 52, 2486-2492; Wang, L.; Zou, J-J.; Zhang, X.; Wang, L. *Energy Fuels* 2011, 25, 1342-1347; Qin, X.; Yue, L.; Wu, J.; Guo, Y.; Xu, L.; Fang W. *Energy Fuels* 2014, 28, 6210-6220; Cao, X.; Qin, X.; Wu, X.; Guo, Y.; Xu, L.; Fang, W. *J. Chem. Eng. Data* 2014, 59, 2602-2613; Qin X.; Cao, X.; Guo, Y.; Xu, L.; Hu, S.; Fang, W. *J. Chem. Eng. Data* 2014, 59, 775-783; Wang, L.; Zhang, X.; Zou, J-J.; Han, H.; Li, Y.; Wang, L. *Energy Fuels* 2009, 23, 2383-2388; Harvey, B. G.; Harrison, K. W.; Davis, M. C.; Chafin, A. C.; Baca, J.; Merriman, W. W. *J. Am. Chem. Soc.* 2016 submitted) The high NHOC imparts improved range to aircraft and ground vehicles, while the high cetane number allows for the use of these fuels in diesel engines. Despite the promise of this class of fuels, previous alkyl adamantanes were directly isolated from petroleum deposits or were synthesized from petroleum-derived multicyclic hydrocarbons.

To explore the potential of cedarwood oil as a high density fuel and develop a method to generate a sustainable alkyl-diamondoid fuel, this paper describes the preparation and characterization of hydrogenated cedarwood oil, a single component fuel containing only cedrane, and a complex mixture of adamantanes prepared by the AlCl$_3$ catalyzed isomerization of cedrane.

Experimental

General. Distilled cedarwood oil was purchased from Penta Manufacturing. α-Cedrol, redistilled, was purchased from Sigma Aldrich and recrystallized from methanol prior to use. The recrystallized product was >95% pure by Gas chromatography-mass spectrometry (GC/MS). Nuclear magnetic resonance spectroscopy (NMR) spectra were collected with a Bruker Avance II 300 MHz NMR spectrometer. $^1$H and $^{13}$C NMR chemical shifts are reported versus the deuterated solvent peak [CDCl$_3$: δ 7.27 ppm ($^1$H), 77.23 ppm ($^{13}$C)]. GC/MS was performed on an Agilent Technologies 6890N network GC system with a 5973 mass selective detector and a 7683 injector. The samples were dissolved in CH$_2$Cl$_2$ and injected at 280° C. The oven was held at 40° C. for 3 minutes and then ramped at a rate of 20° C./min to 300° C. and held for 10 min. Density measurements were made using pre-calibrated floats suspended in the liquid. NHOC was measured as previously described for HCWO and cedrane. The gross heat of combustion of the adamantane mixture was measured by the Southwest Research Institute using ASTM D4089. The NHOC was calculated from the gross value using elemental analysis data. Elemental analysis was carried out by Atlantic Microlab, Inc. (Norcross, Ga.). Viscosity measurements were performed with a Brookfield Engineering DV-11+ Pro viscometer in the temperature range from −20° C. to 40° C. as described previously. Ignition quality testing (IQT) was performed by the Southwest Research Institute. Derived Cetane Numbers (DCNs) were calculated from the ignition delays as described in ASTM D6890. Differential scanning calorimetry (DSC) was performed on a TA Instruments Q100 differential scanning calorimeter using sealed hermetic, aluminum pans under a $N_2$ atmosphere. High purity indium was used to calibrate the calorimeter. Sample sizes were between 2-10 mg. The samples were heated from −80° C. to 50° C. at 10° C./min. (Harvey, B. G.; Merriman, W. W.; Koontz, T. A. *Energy Fuels* 2015, 29, 2431-2436)

Hydrogenation of cedarwood oil. Cedarwood oil (459 g) was added to a 2 L Parr bomb along with glacial acetic acid (200 mL) and $PtO_2$ (2.54 g, 11.2 mmol). The bomb was evacuated and back-filled with hydrogen several times and was then placed under hydrogen pressure (400 psi) and vigorously stirred for 18 h at room temperature followed by an additional 18 h at 120° C. The resulting mixture was then filtered through Celite and washed with water, a 10% aqueous solution of $Na_2CO_3$, and brine. The organic layer was then dried over $MgSO_4$ and filtered.

Synthesis of cedrane. In a typical procedure, α-cedrol (162.4 g, 0.73 mol) was allowed to react with paratoluene-sulfonic acid monohydrate (1.745 g, 9.2 mmol) under refluxing benzene, and the water collected in a Dean-Stark trap. After 4.5 h, approximately 14.5 mL of water had accumulated and production ceased. The solution was extracted with 500 mL each of $H_2O$, aqueous sodium bicarbonate, and brine. The organic layer was dried over $MgSO_4$ and the solvent was removed under reduced pressure to yield a yellow to light red/brown liquid. GC/MS showed virtually complete conversion to α-cedrene. Hydrogenation was carried out in a Parr bottle charged with α-cedrene (450 mL), acetic acid (225 mL), and $PtO_2$ (2.0 g, 8.8 mmol). The mixture was placed under hydrogen pressure (50 psi) and shaken until consumption of hydrogen ceased. The mixture was then filtered through Celite to remove the catalyst and washed with $H_2O$, aqueous sodium bicarbonate, and brine. After drying with $MgSO_4$, removal of the volatiles under reduced pressure yielded a clear liquid with a slight yellow tint. Vacuum distillation yielded a colorless liquid that was >97% pure α-cedrane via GC/MS. $^1H$ NMR (300 MHz, $CDCl_3$), δ 1.87 (sext, J=5.7 Hz, 1H), 1.80-1.61 (m, 5H), 1.57-1.22 (m, 8H), 1.16 (s, 3H), 1.04 (d, J=6.9 Hz, 3H), 0.96 (s, 3H), 0.86 (d, J=7.1 Hz, 3H) $^{13}C$ NMR (75 MHz, $CDCl_3$) δ 58.2, 56.0, 54.6, 47.9, 44.3, 42.6, 38.9, 37.4, 34.1, 29.8, 29.3, 27.5, 25.9, 22.0, 15.7. Anal. Calc for $C_{15}H_{26}$: C, 87.30; H, 12.70. Found: C, 87.59; H, 12.8.

Isomerization of Cedrane. Cedrane (134.14 g, 0.650 mol) was added to aluminum trichloride ($AlCl_3$, 67.07 g, 0.503 mol). Water (0.583 g, 32.4 mmol) was then added dropwise to the rapidly stirring mixture. The slurry was stirred under nitrogen for 3 days at ambient temperature and then heated to 50° C. for an additional day. The mixture was then filtered on a coarse frit and the residual $AlCl_3$ was washed with several aliquots of hexanes. The combined organic fractions were washed with dilute $NaHCO_3$, water, and brine and then dried over $MgSO_4$. After removal of the hexanes under reduced pressure, vacuum distillation (55-60° C., ~0.1 Torr) yielded a colorless liquid that was 90% adamantanes via GC/MS. The predominant product was 1-ethyl-3,5,7-trimethyladamantane (ETMA) at 48% of the total. The adamantane mixture (90% of total) was comprised of ETMA, isomers of ETMA, and 1,3-dimethyladamantane. The other 10% includes various multicyclic hydrocarbons without an adamantane core. $^1H$ NMR ($CDCl_3$): δ 1.13 (q, J=7.6 Hz, 2H), 1.02 (bs, 6H), 0.99 (bs, 6H), 0.89-0.83 (m, 3H), 0.81 (s, 9H). $^{13}C$ NMR (75 MHz, $CDCl_3$) δ 50.8, 47.8, 35.7, 34.8, 31.9, 30.3, 7.2. Anal. Calcd for $C_{15}H_{26}$: C, 87.30; H, 12.70. Found: C, 87.38; H, 12.75.

Results and Discussion

Hydrogenated multicyclic sesquiterpenes have been shown to have volumetric net heats of combustion substantially higher than conventional jet fuels and in some cases rivaling that of the synthetic missile fuel JP-10 which is comprised solely of exo-tetrahydrodicyclopentadiene. (Harvey, B. G.; Merriman, W. W.; Koontz, T. A. *Energy Fuels* 2015, 29, 2431-2436; Bruno, T. J.; Huber, M. L.; Laesecke, A.; Lemmon, E. W.; Perkins, R. A. *Thermochemical and Thermophysical Properties of JP*-10; National Institute of Standards and Technology (NIST): Boulder, Colo., 2006; NISTIR 6640; Harvey, B. G.; Meylemans, H. A.; Gough, R. V.; Quintana, R. L.; Garrison, M. D.; Bruno, T. *J. Phys. Chem. Chem. Phys.* 2014, 16, 9448-9457)

Cedarwood oil (CWO) is a commercially available mixture of multicyclic sesquiterpenes and was used as a promising substrate for the generation of high density fuels. CWO has a variable composition depending on its origin, but the sample used for this study contained 32% α-cedrene, 7% β-cedrene, 51% thujopsene and small amounts of other sesquiterpenes. (Eller, F. J.; King, J. W. *Phytochem. Anal.* 2000, 11, 226-231) To improve the long term stability of the CWO it was hydrogenated in acetic acid with $PtO_2$ under hydrogen (400 psi). GC chromatograms of the starting CWO and hydrogenated CWO (HCWO) can be found in FIG. 1. The hydrogenation of α- and β-cedrenes generates a pair of enantiomers observed as the peak with a retention time of 9.56 min. The hydrogenation of thujopsene has previously been reported to proceed via ring opening and reduction of the cyclopropane ring followed by slow hydrogenation of the trifunctional alkene (FIG. 2). Due to the formation of two new stereocenters, two sets of diastereomers are formed and elute at 9.77 and 9.84 min. Both of these peaks had molecular ions with m/z=208, confirming that two equivalents of $H_2$ had added to thujopsene. Unlike previous reports, thujopsene was also converted to thujopsane, a saturated molecule with the cyclopropane ring intact. The presence of this molecule was observed in the $^1H$ NMR spectrum by a characteristic triplet at 0.01 ppm, doublet of doublet at 0.39 ppm, and singlet at 0.51 ppm. (Bruno, T. J.; Huber, M. L.; Laesecke, A.; Lemmon, E. W.; Perkins, R. A. *Thermochemical and Thermophysical Properties of JP*-10; National Institute of Standards and Technology (NIST): Boulder, Colo., 2006; NISTIR 6640) There are a number of reports in the literature suggesting that dihydrothujopsene and tetrahydrothujopsene are the only products obtained by hydrogenation of thujopsene, but all of these studies used Pd/C as the catalyst at modest pressures. (Hochstetler, A. R. *J. Org. Chem.* 1972, 87, 1883-1886; Forsén, S.; Norin, T. *Acta Chem. Scand.* 1961, 15, 592-598; Norin, T. *Acta Chem. Scand.* 1961, 15, 1676-1694; Schneider, A.; Ware, R. E. 1978 U.S. Pat. No. 4,107,223) It is likely that the use of colloidal platinum as the catalyst and the high pressure (400 psi) used for the reduction favored the formation of thujopsane. This unexpected result is particularly useful for the preparation of a high density fuel. The intact cyclopropane ring should impart a higher NHOC both due to increased density as well as ring strain.

Figure 2:
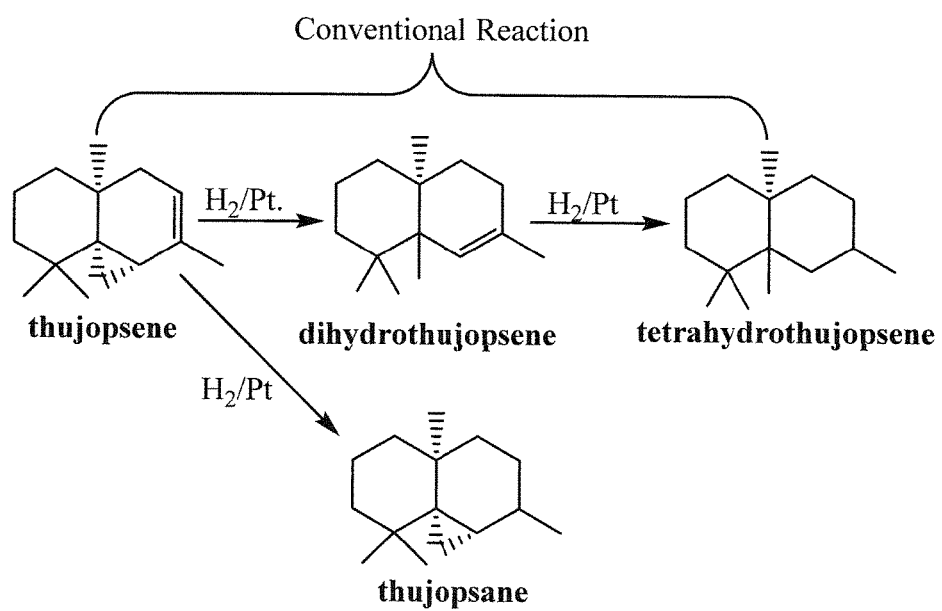
FIG. 2 is a chemical flow chart that shows the hydrogenation of thujopsene, according to embodiments of the invention.

FIG. 1. is a GC Chromatogram of CWO and HCWO. FIG. 2. is a hydrogenation of thujopsene.

With sufficient quantity of HCWO in hand, several fuel properties including density, NHOC, viscosity, DCN, and freezing point were measured. HCWO was found to have a density of 0.917 g/mL, 13% higher than conventional military jet fuel (JP-8) and approaching that of JP-10 (0.935 g/mL). This high density can be attributed to the large percentage of tricyclic sesquiterpanes present in the mixture.

Figure 3:
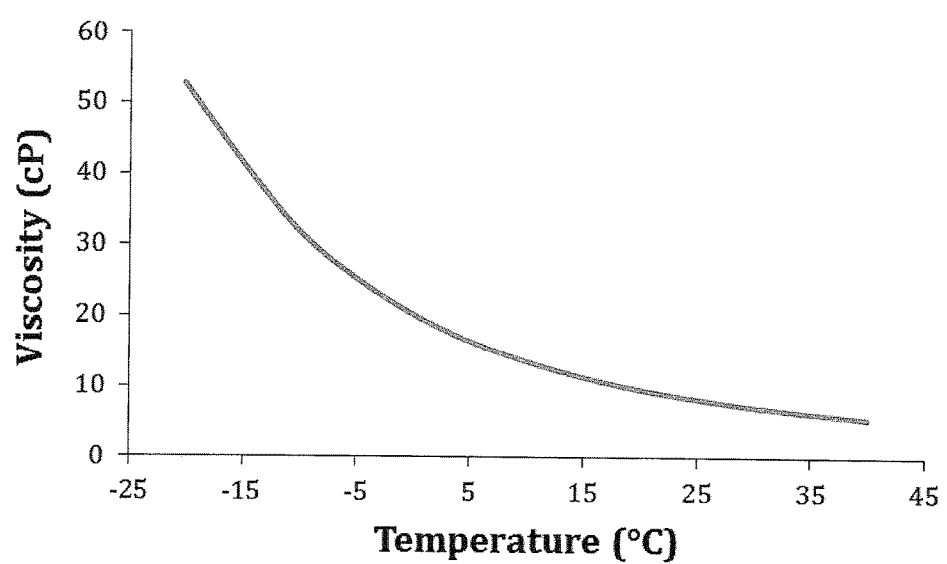
FIG. 3 is a graph showing the dynamic viscosity of HCWO from −20 to 40° C., according to embodiments of the invention.

The U.S. Military use a classification system of Jet Propellant (JP) numbers to describe fuel. JP-8 is a kerosene-based fuel and JP-10 is a gas turbine fuel for missiles. RJ-4 is a liquid rocket propellant used in missiles. The NHOC of HCWO was 140.4 kBtu/gal, more than 12% higher than JP-8 and only 0.8% lower than JP-10. To determine the suitability of HCWO for applications in cold environments, the viscosity was measured from −20 to 40° C. (FIG. 3). The viscosity at −20° C. was more than 54 mm$^2$/s, substantially higher than either JP-8 or JP-10, while the 40° C. viscosity was 6.2 mm$^2$/s, higher than conventional diesel fuel. Despite the relatively high viscosity of HCWO, no freezing point or glass transition temperature was observed even at −80° C. by DSC. To determine the utility of HCWO as a potential diesel fuel, the derived cetane number was measured by Ignition Quality Tester (IQT). Despite the multicyclic structures of the component hydrocarbons, HCWO had a DCN of 31 which is a significant improvement over JP-10 and RJ-4 (Table 1). Although this value is not sufficient for use in a conventional diesel engine, the DCN of HCWO is one of the highest yet observed for multicyclic sesquiterpanes (Table 1). (Harvey, B. G.; Merriman, W. W.; Koontz, T. A. *Energy Fuels* 2015, 29, 2431-2436; Harvey, B. G.; Meylemans, H. A.; Gough, R. V.; Quintana, R. L.; Garrison, M. D.; Bruno, T. J. *Phys. Chem. Chem. Phys.* 2014, 16, 9448-9457)

FIG. 3. Is a dynamic viscosity of HCWO from −20 to 40° C.

TABLE 1

Key Fuel Properties of Multicyclic Fuels

| Fuel | DCN | NHOC (kBtu/gal) |
|---|---|---|
| JP-10 | 20[a] | 141.5[b] |
| RJ-4 | 24[a] | 138.5[c] |
| Caryophyllane[d] | 25 | 132.8[d] |
| Valencane[d] | 23 | 135.4 |
| Premnaspirodiane[d] | 29 | 135.6 |
| IHC-high[e] | 20 | 137.8 |
| IHC-low[e] | 33 | 137.1 |

[a-e](Schneider, A.; Ware, R. E. 1978 U.S. Pat. No. 4,107,223; Bruno, T. J.; Huber, M. L.; Laesecke, A.; Lemmon, E. W.; Perkins, R. A. *Thermochemical and Thermophysical Properties of JP-10*; National Institute of Standards and Technology (NIST): Boulder, CO, 2006; NISTIR 6640; Harvey, B. G.; Merriman, W. W.; Koontz, T. A. *Energy Fuels* 2015, 29, 2431-2436; Harvey, B. G.; Meylemans, H. A.; Gough, R. V.; Quintana, R. L.; Garrison, M. D.; Bruno, T. J. *Phys. Chem. Phys.* 2014, 16, 9448-9457).

Figure 4:
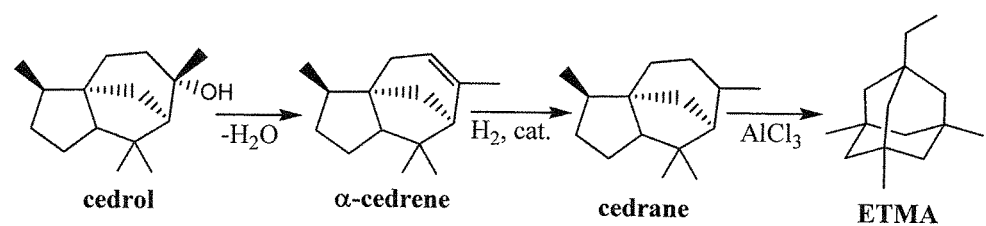
FIG. 4 is a is a chemical flow chart showing the conversion of α-cedrol to ETMA, according to embodiments of the invention.
Figure 5:
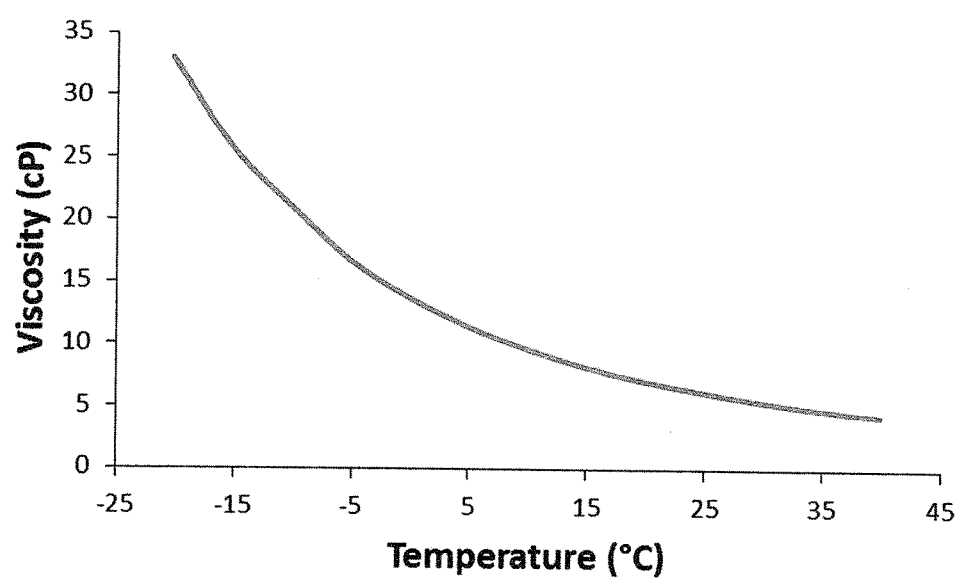
FIG. 5 is a graph showing the dynamic viscosity of cedrane, according to embodiments of the invention.

FIG. 4. is a conversion of α-cedrol to ETMA. FIG. 5. is a dynamic viscosity of cedrane. Given the unique properties of HCWO, it was of interest to obtain pure cedrane to further understand how the different isomers in HCWO affect the fuel properties. α-Cedrol is commercially available and dehydration of α-cedrol with PTSA yielded α-cedrene in excellent yield, while hydrogenation provided analytically pure cedrane (FIG. 4). Cedrane had a density of 0.923 g/mL and a volumetric NHOC of 141.6 kBtu/gal. Both of these values are higher than HCWO and the NHOC of cedrane is virtually identical to that of JP-10 (Table 1). Given the relatively high viscosity of HCWO, and the viscosities of other known tricyclic sesquiterpanes, it was assumed that cedrane would have a similarly high viscosity. Surprisingly, the viscosity of cedrane at −20° C. was only 32 cP (33 mm$^2$/s), while the viscosity at 40° C. was 4.3 cP (4.8 mm$^2$/s) (FIG. 5), approaching the upper limit for conventional diesel fuel. The DCN of cedrane was measured by IQT and found to be only 18, lower than JP-10 and RJ-4. The low cetane number of cedrane suggests that another component of HCWO is responsible for the relatively high cetane number of the mixture. Thujopsane is a likely candidate given that the ring strain of the cyclopropane ring could contribute to a shorter ignition delay. Assuming that the sesquiterpane components of HCWO have similar densities and that the cetane blending effect is roughly linear, the cetane number of the mixture of sesquiterpanes primarily derived from thujopsene is about 39. This is a remarkably high number, particularly for a multicyclic system, and demonstrates that it is feasible to synthesize fuels that have both high densities and high cetane numbers. (Harvey, B. G.; Harrison, K. W.; Davis, M. C.; Chafin, A. C.; Baca, J.; Merriman, W. W. *J. Am. Chem. Soc.* 2016 submitted)

Figure 6:
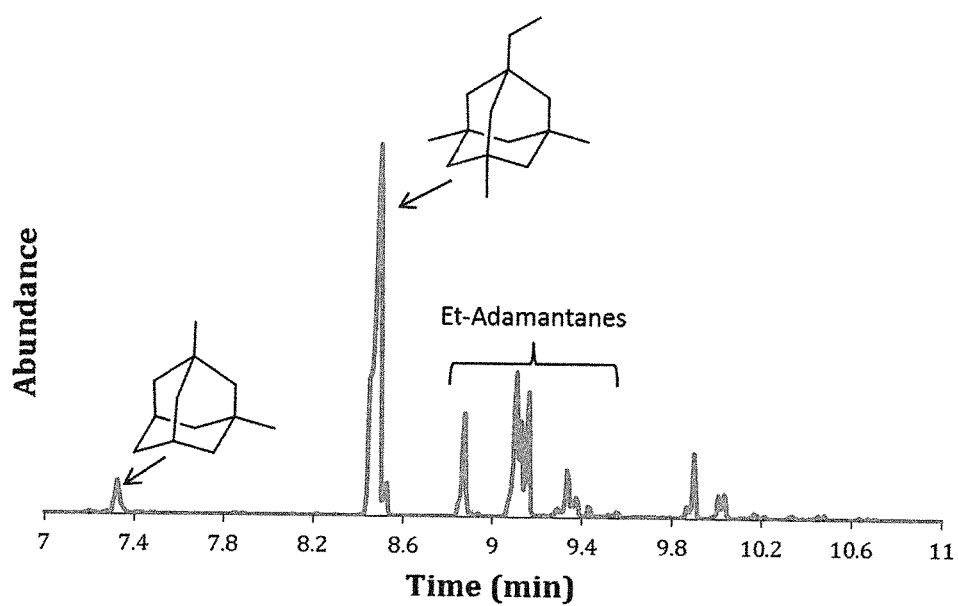
FIG. 6 is a GC chromatogram of the ETMA mixture, according to embodiments of the invention.

With significant quantities of cedrane in hand it was of interest to isomerize it to a mixture of adamantanes by reaction with a strong Lewis acid catalyst. Work by Schleyer in 1966 showed that AlCl$_3$ was an efficient catalyst for isomerization of cedrane to form 1-ethyl-3,5,7-trimethyladamantane (ETMA). (Schleyer, P.; Gleicher, G. J.; Cupas, C. A. *J. Org. Chem.* 1966, 31, 2014-2015) Based on the conversion of the tricyclic cedrane to a tetracyclic adamantane it was hoped that the isomerization would generate a denser hydrocarbon mixture with a higher NHOC. Initially cedrane was allowed to react with fresh AlCl$_3$ under an inert atmosphere. Interestingly, the reaction was extremely sluggish with only traces of adamantanes observed by GC/MS after 24 hour (h). However, it was noticed that an aliquot exposed to air generated the adamantanes quite rapidly. This difference in reactivity suggested that adventitious water was necessary for the reaction to proceed. Addition of ~5 mol % water promoted the reaction and cedrane underwent >90% conversion to a mixture of adamantanes (FIG. 6). In contrast to Schleyer's report, the product distribution was composed of 91% adamantanes and 9% isomerized sesquiterpanes. The adamantane fraction included 3.6% 1,3-dimethyladamantane, 48.6% ETMA, and 38.7% of mixed adamantanes with m/z=206. The mixed adamantanes all appear to be structural isomers of ETMA based on both the molecular ion peak and the presence of large peaks with m/z=177 which represents loss of an ethyl group.

Figure 7:
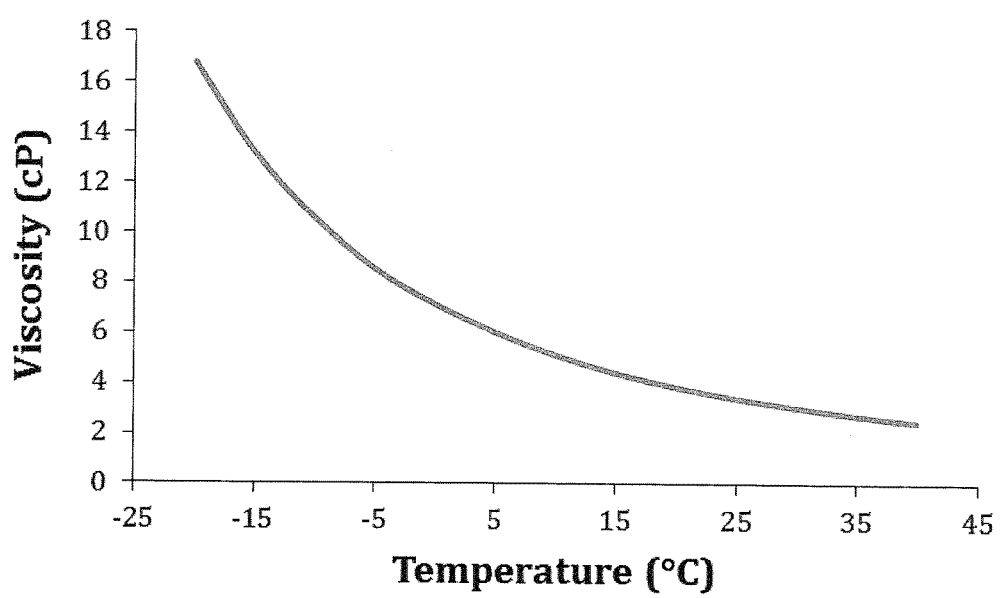
FIG. 7 is a graph showing the dynamic viscosity of ETM from −20 to 40° C., according to embodiments of the invention.

FIG. 6 is a GC chromatogram of the ETMA mixture. FIG. 7. Is a dynamic viscosity of ETMA from −20 to 40° C.

TABLE 2

Key fuel properties of HCWO, cedrane, ETMA, and conventional military fuels

| Fuel | Density (g/mL) | NHOC (kBtu/gal) | Viscosity (mm$^2$/s, −20° C.) | Viscosity (mm$^2$/s, 40° C.) | DCN |
|---|---|---|---|---|---|
| HCWO | 0.917 | 140.4 | 54 | 6.2 | 31 |
| Cedrane | 0.923 | 141.6 | 33 | 4.8 | 18 |
| ETMA | 0.896 | 135.6 | 18 | 2.8 | 46 |
| JP-8 | ~0.81 | ~125 | <8.0 | NA | |
| F-76 | ~0.84 | ~129 | NA | 1.7-4.3 | >42 |

Despite the tetracyclic core structures present in the ETMA mixture, the fuel blend only had a density of 0.896 g/mL. Although this result was surprising, the density of ETMA is quite similar to 1,3-dimethyladamantane which has a density of 0.9016 g/mL. (Qin, X.; Yue, L.; Wu, J.; Guo, Y.; Xu, L.; Fang W. *Energy Fuels* 2014, 28, 6210-6220) The decreased density of ETMA resulted in a decreased volumetric NHOC of 135.6 kBtu/gal, more than 4% lower than cedrane, but 8.5% higher than JP-8 and 5% higher than conventional diesel fuel (Table 2). The unique structure of the adamantanes present in the ETMA mixture also resulted in a significant decrease in viscosity, with a −20° C. viscosity of only 16.8 cP (18 mm$^2$/s) and a 40° C. viscosity of less than 2.5 cP (2.8 mm$^2$/s) (FIG. 7). The viscosity of ETMA is significantly lower than 1-ethyladamantane, but slightly higher at room temperature compared to 1,3-dimethyladamantane. (Qin, X.; Yue, L.; Wu, J.; Guo, Y.; Xu, L.; Fang W. *Energy Fuels* 2014, 28, 6210-6220) ETMA exhibits a dramatically lower viscosity compared to several reported multicyclic sesquiterpanes. (Harvey, B. G.; Meylemans, H. A.; Gough, R. V.; Quintana, R. L.; Garrison, M. D.; Bruno, T. J. *Phys. Chem. Phys.* 2014, 16, 9448-9457) The DCN of ETMA was 46, a remarkable result given the tetracyclic and highly branched structures of the molecules in the mixture. In line with recent studies on alkyl adamantane model compounds, it appears that the adamantane core is responsible for the high cetane number of ETMA.

Conclusions

Three new high density renewable fuels have been prepared from components of cedarwood oil. These fuels exhibit NHOCs substantially higher than conventional jet or diesel fuel, while the viscosity of the fuels can be dramatically reduced by acid catalyzed isomerization. Despite the multicyclic structures of the hydrocarbons comprising the fuel blends, the DCN for HCWO is one of the highest yet observed for a high density sesquiterpane mixture, while the DCN of ETMA is high enough to allow for efficient combustion in a diesel engine. This remarkable result shows that it is possible to create sustainable fuels that have both exceptional densities and high cetane numbers. Unlike traditional biofuels that exhibit lower performance than petroleum based fuels, the fuels described in this work have the potential to outperform conventional fuels. In concert with recent advances in metabolic engineering, the generation of multicyclic sesquiterpenes including α-cedrene and thujopsene from biomass sugars may allow for the production of these fuels on a commercial scale.

The conversion of renewable, bio-derived sesquiterpenes and other isoprenoids to high density diamondoid fuels include alkyl-adamantane fuels where the resulting fuels have net heats of combustion higher than conventional petroleum based fuels. The invention also generally relates to higher terpenes, including diterpenes and triterpenes, and to functionalized isoprenoids, but not limited to terpene alcohols, aldehydes, and epoxides, which can also be converted to high-density diamondoid fuels. High density fuels with improved volumetric net heats of combustion (NHOC) compared to conventional fuels can significantly increase the range, loiter time, or payload of a variety of platforms including missiles, aircraft, and unmanned systems. Embodiments of the invention describe a process for the conversion of renewable, bio-derived sesquiterpenes to high density diamondoid fuels. The resulting fuels have net heats of combustion higher than conventional petroleum based fuels.

Diamondoids are polycyclic hydrocarbons. Alkyl diamondoids (for example, alkyl-adamantanes) are very attractive for use as high-density fuels due to their high densities, low freezing points, and low viscosities. Renewable fuels based on acyclic hydrocarbons typically have densities that are below the specifications for common aviation and military fuels including Jet-A, JP-5, JP-8, and F-76. The resulting decrease in volumetric net heat of combustion limits the range, loiter time, and payload of both commercial and military aircraft, as well as missiles, UAVs, and other platforms. Embodiments of the invention describe methods to generate fuels with properties that meet or exceed those of conventional petroleum derived fuels. Embodiments of the invention describe methods to generate dense, alkylated, multi-cyclic diamondoid fuels from bio-derived sesquiterpenes. This process can be conducted with both heterogeneous and homogenous catalysts. The resulting multi-cyclic structures have densities and volumetric net heats of combustion that are significantly higher than state-of-the-art fuels, while maintaining low viscosities which allow for use at low temperature/high altitude. Moreover, bio-derived sesquiterpenes can be produced from renewable biomass sources. Use of these fuels will decrease Navy dependence on fossil fuels and will also reduce net carbon emissions.

Figure 8:
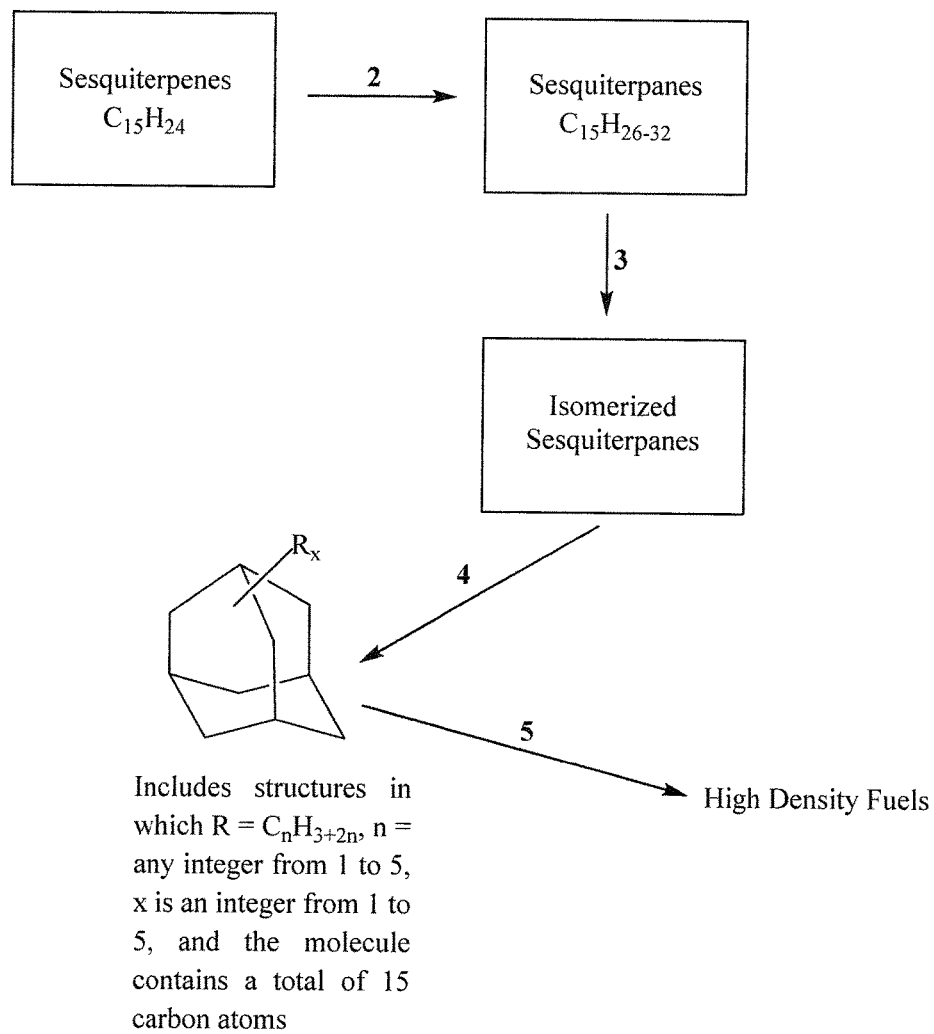
FIG. 8 is a flow chart showing a chemical scheme for conversion of sesquiterpenes to diamondoid fuels, according to embodiments of the invention.

A general chemical scheme for converting isoprenoids to diamondoid fuel is illustrated in FIG. 8 using sesquiterpenes as an example. The chemistry is as follows. The sesquiterpenes are hydrogenated to generate saturated hydrocarbons. When the isoprenoids are hydrogenated tricyclic sesquiterpenes, they will have the formula $C_{15}H_{26}$; hydrogenated bicyclic sesquiterpenes will have the formula $C_{15}H_{28}$; hydrogenated monocyclics will have the formula $C_{15}H_{30}$ and hydrogenated acyclic sesquiterpenes will have the formula $C_{15}H_{32}$. The saturated hydrocarbons are then isomerized with an acidic catalyst to produce diamondoid fuel. The diamondoid fuel is purified, and/or various cuts are removed for specific applications, by distillation. The distilled fuel is used directly or is formulated/blended for specific fuel applications. For example, the alkyl-adamantane fuels of the invention may be blended with, but not limited to, Jet A, JP-10, JP-5, F-76, other renewable fuels including fuels derived from biobutene, biohexene, etc. The alkyl-adamantane fuels that are embodiments of the invention will normally be a mixture of various alkyl-adamantanes and sesquiterpanes. The amount of sesquiterpane may be in the range of about 1% to 90% of the alkyl-adamantane fuel.

Sesquiterpenes are isolated from a renewable source. Sesquiterpenes can be generated by a biosynthetic process that utilizes sugar, biomass sugars, $CO_2$, or CO as a carbon source. Synthetic sesquiterpenes can be used and prepared directly from isoprene or from a reaction between terpenes and isoprene. Alternatively, sesquiterpenes can be extracted from plants using processes that include steam distillation and solvent extraction. Sesquiterpenes can be acyclic. Sesquiterpenes can be mono-cyclic and/or polycyclic hydrocarbons. Cyclic sesquiterpenes can be generated from acyclic sesquiterpenes.

Higher terpenes including diterpenes and triterpenes, can be thermally cracked to form sesquiterpenes. Examples of bio-derived sequiterpenes that are feedstocks embodied in the invention are, but not limited to, farnesene, cadinene, selinene, humulene, copaene, cloven, alpha-neoclovene, longifolene, zizaene, thujopsene, other tricyclic sesquiterpenes, caryophyllene, isomerized caryophyllene mixtures, other bicyclic sesquiterpenes, monocyclic sesquiterpenes including bisabolene, and acyclic sesquiterpenes including farnesene. Bio-derived cyclopentadiene dimers and higher oligomers of bio-derived cyclopentadienes are also disclosed which includes alkylated versions (i.e. tetrahydrodimethyldicyclopentadiene) which we have shown can be generated from linalool, myrcene, and some sesquiterpenes.

The following are publications related to topics of the invention. The basic properties of petroleum-derived diamondoid-type fuels are described in: Chung, H. S.; Chen, C. S. H.; Kremer, R. A.; Boulton, J. R.; Burdette, G. W. Energy Fuels 1999, 13, 641-649. A recent paper has described the conversion of functionalized, hydrogenated cyclopentadienes to diamondoid fuels with ionic liquids: Ma, T.; Feng, R.; Zou, J-J.; Zhang, X.; Wang, Li Industrial and Engineering Chemistry Research 2013, 52, 2486-2492.

Isoprenoid feedstocks, including sesquiterpenes, are hydrogenated to generate saturated hydrocarbons. The hydrogenations can be conducted with either homogenous or heterogeneous catalysts under a hydrogen atmosphere. Hydrogenation catalysts based on nickel, palladium, platinum, ruthenium, and copper are suitable for the reduction. This can typically be conducted without a solvent. Hydrogenations may be conducted with or without a solvent. In some embodiments, addition of a polar solvent increases the reaction rate and allows for the use of milder conditions.

The saturated hydrocarbons are isomerized with acidic catalysts, including a strong Lewis acid or Bronsted acid. Examples of suitable Lewis acid catalysts include $AlCl_3$ and ionic liquids derived from or including $AlCl_3$. Heterogenous Lewis acid catalysts, mesoporous aluminosilicates (e.g. AlMCM-41), and amorphous aluminosilicates, can also be used. Lewis acidic ionic liquids and fluorinated sulfonic acids (heterogeneous and homogenous) are also suitable acidic catalysts for the isomerization.

When heterogeneous catalysts are used in a liquid-phase reaction, the hydrocarbon mixture may be separated by filtration, centrifugation, decantation and/or purified by distillation. In the case of homogenous catalysis, the catalyst may be quenched and the hydrocarbon may be separated by extraction and/or purified by distillation.

Purified alkyl-adamantane fuels may be used directly as high-density fuels or formulated with various conventional or renewable fuels to generate full-performance jet and diesel fuels.

Figure 9:
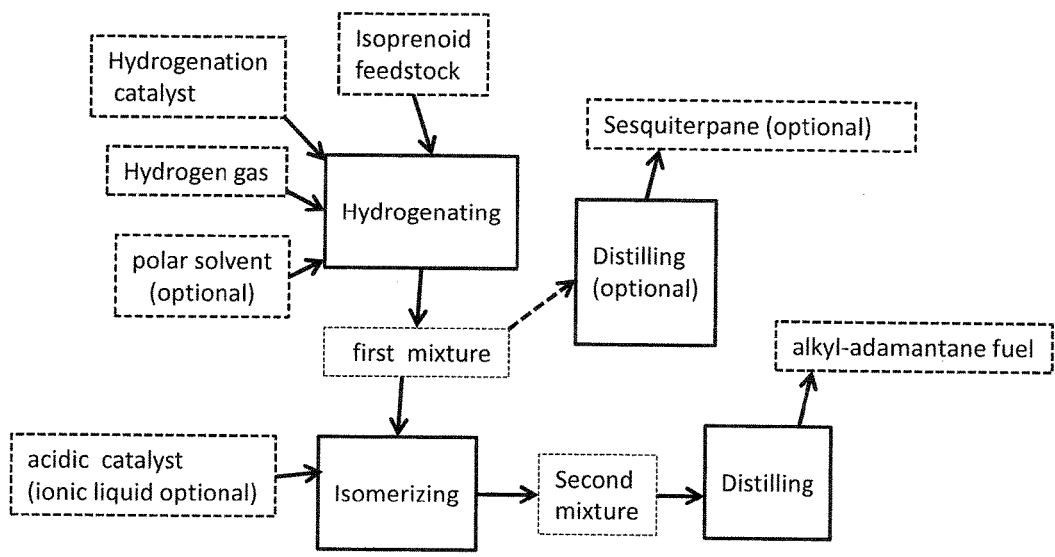
FIG. 9 is a flow chart for producing alkyl-adamantane fuel, according to embodiments of the invention.

The method shown in FIG. 9 shows a general method for converting an isoprenoid and/or functionalized isoprenoid feedstock to an alkyl-adamantane fuel. A first mixture is produced by hydrogenating the feedstock from about 1 to 48 hours with hydrogen gas at pressures ranging from about 1 atm to about 50 atm using a hydrogenation catalyst at temperatures ranging from about 10° to 200° C. An optional polar solvent may be used in the hydrogenation reactor or hydrogenation reaction zone. The first mixture may optionally be distilled to isolate hydrogenated fuel products, including a sesquiterpane. The first mixture is isomerized producing a second mixture. The isomerizing is carried out from about 0.3 to 48 hours using an acidic catalyst at pressures ranging from about 1 atm to about 10 atm at temperatures ranging from about 15° C. to 350° C. The isomerized second mixture is distilled to produce an alkyl-adamantane fuel, which is a mixture of alkyl-adamantanes and isomerized sesquiterpanes, or the second mixture is distilled to produce specific aklyadamantanes and/or specific isomerized sesquiterpanes.

Lewis acids, including acidic ionic liquids, are used to isomerize hydrogenated polycyclic hydrocarbons, including endotetrahydrodicyclopentadiene (endo-THDCPD) to exo-THDCPD, which is the major component of the synthetic fuel called JP-10. Furthermore, both endo- and exo-THDCPD can be converted to adamantane, the simplest diamondoid, via skeletal rearrangement (isomerization) using aluminum trichloride ($AlCl_3$) as the Lewis acid. The molar fraction of $AlCl_3$ in the ionic liquid determines the acidity of the solvent. Increasing the temperature of the reaction increases the reaction rate and can affect the percent conversion, selectivity, and ratios of various products obtained. A reasonable temperature range for the reaction is from 30° to 120° C. The fact that ionic liquids phase separate from nonpolar hydrocarbons make ionic-liquid-based methods suitable for continuous flow reaction systems.

Figure 10:
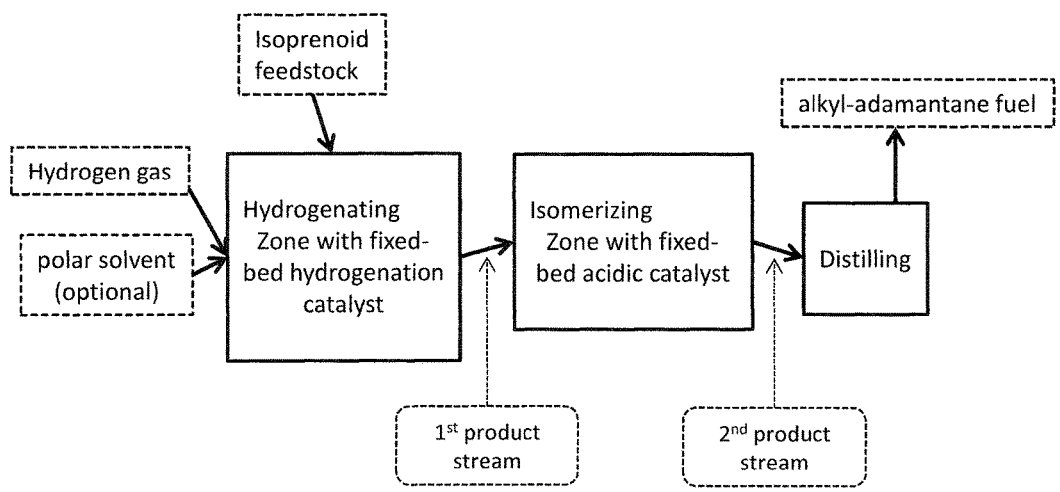
FIG. 10 is a continuous-flow chart for producing alkyl-adamantane fuel, according to embodiments of the invention.

A continuous-flow process for producing alkyl-adamantane fuel is an embodiment of the invention. The continuous-flow method shown in FIG. 10 uses an isoprenoid and/or substituted isoprenoid feedstock, which may include sesquiterpenes. The feedstock is hydrogenated with hydrogen gas using a heterogeneous hydrogenation catalyst to produce first product stream, which is then isomerized using a heterogeneous acidic catalyst to produce a second product stream. The second product stream is distilled to produce an alkyl-adamantane fuel. The catalysts of the continuous-flow method are supported on fixed beds located in the respective zones. An optional polar solvent may be used, and is fed into the hydrogenating and isomerizing zone. The first product stream is produced by hydrogenating the feedstock having a residence time in the hydrogenation zone from about 0.5 to 48 hours with hydrogen gas at pressures ranging from about 1 atm to about 50 atm at temperatures ranging from about 10° C. to 200° C. The first product stream enters the isomerizing zone. The residence time in the isomerizing zone is about 0.2 to 48 hours at pressures ranging from about 1 atm to about 10 atm and at temperatures ranging from about 15° C. to 350° C. The second product stream exiting the isomerizing zone is distilled to produce an alkyl-adamantane fuel. When an ionic liquid is used, since it is insoluble in the nonpolar hydrocarbon products formed, it may be isolated from the fuel products and recycled back to the isomerizing zone. Optionally, a solid-state crosslinked ionic liquid-like material may be attached to a fixed bed in the isomerizing zone.

Example 1 n-Butyl-1-adamantaneketone 20 g of 1-adamantane carboxylic acid was dissolved in 250 mL THF and then cooled to −20° C. and while cold 93 mL 2.5 M n-BuLi (2.1 equiv) was added slowly dropwise over 1 h. Solids precipitated during this time and then the mixture was stirred at rt overnight. A standard workup generated 20.8 g crude oil. The product was further purified by distillation under reduced pressure. $^1H$ ($CDCl_3$): 2.44 (t, J=7.1 Hz, 2H), 2.04 (m, 3H), 1.9-1.63 (m, 12H), 1.59-1.43 (m, 2H), 1.36-1.21 (m, 2H), 0.90 (t, J=7.7 Hz, 3H); 13C (CDCl3): 215.84, 46.45, 38.39, 36.78, 35.76, 28.16, 25.98, 22.62, 14.10. Analysis calcd for $C_{15}H_{24}O$: C, 81.76; H, 10.98. Found: C, 81.71; H, 11.00.

1-Pentyladamantane 2.3 g of n-butyl-1-adamantane ketone, 5 g hydrazine hydrate, 20 mL of diethylene glycol, and 5.6 g KOH were heated to 220° C. for 1 h, brought down to 180° C. for 3 h and then left overnight at 130° C. After a standard workup, this procedure gave 2.43 g of crude product (92%). Reduced pressure distillation gave the compound as a colorless liquid. When the reaction was conducted at ten times the scale, a yield of 97% was obtained. The product doesn't freeze when stored at −30° C. $^1H$ ($CDCl_3$): 1.93 (m, 3H), 1.79-1.52 (m, 6H), 1.49-1.43 (m, 6H), 1.37-1.17 (m, 6H), 1.07-0.97 (m, 2H), 0.89 (t, J=7.2 Hz, 3H); 13C (CDCl3): 45.03, 42.82, 37.60, 33.17, 32.48, 29.08, 22.98, 22.29, 14.36. Analysis calcd for $C_{15}H_{26}$: C, 87.3; H, 12.7. Found: C, 87.14; H, 12.75.

Example 2

1-Pentyl adamantane, as an example of an alkyl-adamantane fuel, an embodiment of the invention, has a density of 0.946 g/mL, and a net heat of combustion (NHOC), measured by bomb calorimetry, of 145,997 btu/gal (relative standard deviation of 1.3%).

Example 3

Typical hydrogenation conditions for sesquiterpenes. Hydrogenation of sesquiterpenes including β-caryophyllene, valencene, and premnaspirodiene was conducted in a Parr shaker without the addition of solvent at room temperature and with an overpressure of 40-50 psi of hydrogen. Either 1 g of 10% Pd/C or 0.1 g of $PtO_2$ was used for every 100 g of sesquiterpene. The bomb was shaken until uptake of hydrogen ceased. The hydrogenation of valencene and premnaspirodiene was complete within two hours, while caryophyllene typically required up to 48 hours to fully react. After hydrogenation was complete, the black reaction mixtures were then filtered through a celite pad. Valencane, premnaspirodiane, and caryophyllene were used directly without further purification or were vacuum distilled (85-110° C., 1 Torr) through a 10 in Vigreux column to isolate the hydrogenated sesquiterpenes as colorless oils.

Example 4

Hydrogenation of Longifolane: 100 mL of longifolene, 30 mL of glacial acetic acid, and 0.1 g of PtO2 were added to a glass bomb. The bomb was placed under 45 psi hydrogen and shaken at room temperature for two h. The acetic acid was removed in a separatory funnel and the longifolane was washed with water (2×20 mL) and a 5% sodium carbonate solution. The longifolane was then purified by vacuum distillation.

Example 5

Hydrogenated sesquiterpanes are combined with an acid catalyst. The catalyst loading, reaction time, and temperature are dependent on the catalyst type. Some general reaction conditions are listed in Table 3. All reactions are conducted under an inert atmosphere and products were purified by either physical separation (heterogeneous catalysts) or quenching/extraction (homogenous catalysts) followed by isolation of either diamondoids or diamondoid/isomerized sesquiterpane mixtures by fractional distillation.

TABLE 3

Common reaction conditions for isomerization of sesquiterpanes to diamondoid fuels

| Catalyst | Temp (° C.) | Time |
| --- | --- | --- |
| $AlCl_3$ | 150-200 | 2-4 h |
| Acidic ionic liquid | 80-120 | 10 min-several h |
| Heterogeneous catalyst | up to 350° C. | 1-5 h |

Prophetic examples are for illustration purposes only and not to be used to limit any of the embodiments. Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Embodiments of the invention generally relate to methods for synthesizing first alkyl-adamantane fuel including, providing a first isoprenoid and/or functionalized isoprenoid feedstock, producing first mixture by hydrogenating the first feedstock with hydrogen gas using at least one first hydrogenation catalyst, producing a second mixture by isomerizing the first mixture from about 0.3 hours to about 48 hours using a first acidic catalyst, and distilling the second mixture to produce the first alkyl-adamantane fuel. Another aspect of the invention generally relates to continuous-flow methods for synthesizing second alkyl-adamantane fuel including, providing second isoprenoid and/or functionalized isoprenoid feedstock, hydrogenating the second feedstock with hydrogen gas using second hydrogenation catalyst to produce first product stream, isomerizing the first product stream using second acidic catalyst to produce second product stream, and distilling the second product stream to produce the second alkyl-adamantane fuel.

In embodiments, in producing the first mixture the hydrogenation catalyst further includes at least one transition-metal selected from the group consisting of, but not limited to, nickel, palladium, platinum, ruthenium, and copper. In embodiments, in producing the first mixture, the hydrogenating further includes adding at least one polar solvent selected from the group consisting of, but not limited to, ethyl acetate, other organic ester, acetic acid, other organic acid, methanol, ethanol, butanol, THF, dioxane, and other alcohols and alcohols. In embodiments, the producing the first mixture further includes distilling the first mixture to produce at least one sesquiterpane. In embodiments, the homogeneous acidic catalyst is selected from the group consisting of, but not limited to, $AlCl_3$, $FeCl_3$, $TiCl_4$, $ZnCl_2$, $SbF_5$, $BF_3$, Lewis acids based on Ti, V, Cr, Mn, Fe, Co, Ni, Cu, Zn, Al, B, Sn, Sb in various oxidation states, and other homogeneous Lewis-acid compounds.

In embodiments, the producing the second mixture by isomerizing further includes adding at least one ionic liquid selected from the group consisting of, but not limited to, pyridinium ionic liquid, imidazolium ionic liquid, acidic ionic liquid, acidic chloroaluminate ionic liquid, clay-supported chloroaluminate ionic liquid, [1-butyl-3-methylimidazolium][bis(trifluoromethylsulfonyl imide)], [1-butyl-3-methylimidazolium][tricyanomethanide], [tri(butyl)(tridecyl)phosphoniumlibis(trifluoro methylsulfonyl imide)], triethylammonium chloroaluminate, [1-butyl-3-methylpyridinium] chloroaluminate, and [1-butyl-3-methyl-imidazolium] chloroaluminate. In embodiments, the acidic catalyst is a heterogeneous Lewis-acid selected from at least one of the group consisting of, but not limited to, $AlCl_3$, $FeCl_3$, $TiCl_4$, $ZnCl_2$, $SbF_5$, $BF_3$, Lewis acids based on Ti, V, Cr, Mn, Fe, Co, Ni, Cu, Zn, Al, B, Sn, Sb in various oxidation states, and other Lewis-acid compound, and where the heterogeneous acidic catalyst is supported on at least one solid material selected from the group consisting of, but not limited to, zeolite, aluminosilicate, alumina, zirconia, titania, silica, and clay, other acidic metal oxide, cross-linked sulfonated polystyrene, other macroreticular resin, other polymer, crosslinked ionic liquid, crosslinked poly(ionic liquid), and crosslinked ionic liquid gel.

In embodiments, the producing the first mixture by hydrogenating the first feedstock is from about 1 hour to 48 hours with hydrogen gas at pressures ranging from about 1 atm to about 50 atm using the first hydrogenation catalyst at temperatures ranging from about 10° C. to 200° C. and where the producing the second mixture by isomerizing the first mixture is from about 0.3 hour to about 48 hours using the first acidic catalyst at pressures ranging from about 1 atm to about 10 atm at temperatures ranging from about 15° C. to about 350° C. In embodiments, the first alkyl-adamantane fuel produced by the methods herein are included in a blended fuel including, but not limited to, Jet A, JP-10, JP-5, F-76, butene oligomer fuels, and hexene oligomer fuels. In embodiments, the hydrogenating the second feedstock with the second hydrogenation catalyst is a heterogeneous second hydrogenation catalyst supported on a fixed bed.

In embodiments, the hydrogenating further includes adding at least one polar solvent selected from the group consisting of, but not limited to, ethyl acetate, other organic ester, acetic acid, other organic acid, methanol, ethanol, butanol, and other alcohols. In embodiments, the isomerizing the first product stream of the second acidic catalyst is a heterogeneous second Lewis acid supported on a fixed bed. In embodiments, the first alkyl-adamantane fuel is produced by the methods herein is a blended fuel including Jet A, JP-10, JP-5, F-76, butene oligomers, and hexene oligomers. In other embodiments, the second alkyl-adamantane fuel being 1-pentyl adamantane is produced by the methods herein are a blended fuel including Jet A, JP-10, JP-5, F-76, biobutene, and biohexene.

In embodiments, the blended fuel has a density of at least 0.90 g/mL and a NHOC of at least 135,000 Btu/gal. In embodiments, the fuel has a cetane number ranging from about 30 to about 42. In embodiments, the blended fuel has a cetane number ranging from about 42 to about 50 and has from about 1% to about 70% of the alkyl-adamantane fuel. The cedarwood oil can be hydrogenated without any solvent, in solution, or biphasic.

Embodiments of the invention generally relates to method for converting cedarwood oil into high density fuels including, hydrogenating cedarwood oil in the presence of at least one hydrogenation catalyst to generate hydrogenated cedarwood oil, removing the hydrogenation catalyst from the hydrogenated cedarwood oil, purifying the hydrogenated cedarwood oil to produce first high density fuels, isomerizing the first high density fuel in the presence of at least one acid catalyst to generate a hydrocarbon mixture including adamantanes, and distilling the adamantane mixture to produce second alkyl-adamantane high density fuels. Other embodiments include methods for converting tricyclic sesquiterpenes into high density fuels including, hydrogenating single components or blends of thujopsene, alpha-cedrene, beta-cedrene with at least one hydrogenating catalyst to produce saturated or hydrogenated sesquiterpanes, removing the hydrogenation catalyst from the saturated or hydrogenated sesquiterpanes, purifying the hydrogenated sesquiterpanes to produce first high density fuels, isomerizing the first high density fuels in the presence of at least one acid catalyst to generate a hydrocarbon mixture including adamantanes, and distilling the adamantine mixtures to produce second high density fuels.

Yet other embodiments include methods for converting tricyclic sesquiterpenes into high density fuels including, dehydrating cedrol or epi-cedrol with at least one acid catalyst to generate alpha cedrene, hydrogenating single components or blends of thujopsene, alpha-cedrene, beta-cedrene to produce saturated or hydrogenated sesquiterpanes, removing the hydrogenation catalyst from the saturated or hydrogenated sesquiterpanes, purifying the hydrogenated sesquiterpanes to produce first high density fuels, isomerizing the first high density fuels in the presence of at least one acid catalyst to generate a hydrocarbon mixture including adamantanes, and distilling the adamantine mixtures to produce second high density fuels.

In embodiments, the hydrogenated cedarwood oil has a cetane number in the range of about 25 to about 50. In embodiments, hydrogenating cedarwood oil is utilizing hydrogen pressure and an optional polar solvent. In embodiments, the acid catalyst is selected from the group including $AlCl_3$, $AlBr_3$, transition metal triflates, main group metal/metalloid triflates, and Lewis acidic ionic liquids. In embodiments, at least one catalyst is a heterogeneous Lewis acid. In other embodiments, at least one hydrogenation catalyst is based on selected from the group comprising Pt, Pd, Ni, Cu, and Zn. Embodiments further include distilling the first high density duel to produce sesquiterpanes. In other embodiments, the method of producing the first and second high density fuels is a continuous process.

In embodiments, the source of alpha cedrene is generated by dehydration of cedrol or epi-cedrol. Further embodiments include hydrogenating the alpha-cedrene to generate cedrane, and isomerizing the cedrane with at least one second acid catalyst to generate 1-ethyl-3,5,7,-trimethyladamantane, adamantanes with molecular weight of about 206 g/mol, 1,3-dimethyladmantane, and a mixture of alkyl adamantanes having a cetane number in the range from about 40-50. Further embodiments include hydrogenating the thujopsene under hydrogen atmosphere with a Pt-based catalyst to produce 20-100% thujopsane having a cetane number in the range of about 35 of about 45. In embodiments, the hydrogenating of the alpha-cedrene, beta-cedrene, and/or thujopsene is conducted at pressures between 30 and 5000 psi to promote efficient hydrogenation of the double bond in the thujopsene while keeping the cyclopropane ring of thujopsene intact. In embodiments, the hydrogenating of the alpha-cedrene, beta-cedrene, and/or the thujopsene is conducted at pressures between 1000 and 5000 psi. In embodiments, at least one first hydrogenation catalyst is heterogeneous. In embodiments, at least one first hydrogenation catalyst includes $PtO_2$, platinum nanoparticles supported on a heterogeneous support, and palladium supported on a carbon support. In embodiments, the hydrogenating alpha-cedrene, beta-cedrene, and/or thujopsene is utilizing hydrogen pressure and an optional polar solvent. In embodiments, the hydrogenation catalyst is a heterogeneous hydrogenation catalyst.

Another aspect of the invention includes hydrogenated cedarwood oil produced by the methods herein. Yet another aspect of the invention includes first and/or second high density fuels produced by the methods herein.

Patent application Ser. No. 14/311,588 filed on Jun. 23, 2014, describes the conversion of sesquiterpenes to diamondoid fuels and is incorporated by reference. Patent application Ser. No. 15/297,285 filed on Oct. 19, 2016, describes the processes for the conversion of renewable, bio-derived sesquiterpenes to high density diamondoid fuels, and the resulting fuels have net heats of combustion higher than conventional petroleum based fuels and is incorporated by reference. Patent application Ser. No. 15/099,190 filed on Apr. 14, 2016 describes methods for the conversion of vegetable oils into high density fuels with net heats of combustion in excess of 135,000 btu/gal and densities in excess of 0.89 g/mL. The invention further details a method for generating high density fuels suitable for combustion in a diesel engine and is incorporated by reference. Petroleum Chemistry 2011, 51, 331-335 describes conversion of triglycerides to alkyladamantanes. Energy and Fuels 1999, 13, 641-649 describes some properties of petroleum-derived, complex adamantane mixtures.

High density fuels with improved volumetric net heats of combustion (NHOC) compared to conventional fuels can significantly increase the range, loiter time, or payload of a variety of platforms including missiles, aircraft, and unmanned systems. Embodiments of the invention describe a process for the conversion of renewable, bio-derived sesquiterpenes to high density diamondoid fuels. The resulting fuels have net heats of combustion higher than conventional petroleum based fuels.

Diamondoids are polycyclic hydrocarbons. Alkyl diamondoids (for example, alkyl-adamantanes) are very attractive for use as high-density fuels due to their high densities, low freezing points, and low viscosities. Renewable fuels based on acyclic hydrocarbons typically have densities that are below the specifications for common aviation and military fuels including Jet-A, JP-5, JP-8, and F-76. The resulting decrease in volumetric net heat of combustion limits the range, loiter time, and payload of both commercial and military aircraft, as well as missiles, UAVs, and other platforms. Embodiments of the invention describe methods to generate fuels with properties that meet or exceed those of conventional petroleum derived fuels. Embodiments of the invention describe methods to generate dense, alkylated, multi-cyclic diamondoid fuels from bio-derived sesquiterpenes. This process can be conducted with both heterogeneous and homogenous catalysts. The resulting multi-cyclic structures have densities and volumetric net heats of combustion that are significantly higher than state-of-the-art fuels, while maintaining low viscosities which allow for use at low temperature/high altitude. Moreover, bio-derived sesquiterpenes can be produced from renewable biomass sources. Use of these fuels will decrease Navy dependence on fossil fuels and will also reduce net carbon emissions.

A general chemical scheme for converting isoprenoids to diamondoid fuel is using sesquiterpenes as an example. The chemistry is as follows. The sesquiterpenes are hydrogenated to generate saturated hydrocarbons. When the isoprenoids are hydrogenated tricyclic sesquiterpenes, they will have the formula $C_{15}H_{26}$; hydrogenated bicyclic sesquiterpenes will have the formula $C_{15}H_{28}$; hydrogenated monocyclics will have the formula $C_{15}H_{30}$ and hydrogenated acyclic sesquiterpenes will have the formula $C_{15}H_{32}$. The saturated hydrocarbons are then isomerized with an acidic catalyst to produce diamondoid fuel. The diamondoid fuel is purified, and/or various cuts are removed for specific applications, by distillation. The distilled fuel is used directly or is formulated/blended for specific fuel applications. For example, the alkyl-adamantane fuels of the invention may be blended with, but not limited to, Jet A, JP-10, JP-5, F-76, other renewable fuels including fuels derived from biobutene, biohexene, etc. The alkyl-adamantane fuels that are embodiments of the invention will normally be a mixture of various alkyl-adamantanes and sesquiterpanes. The amount of sesquiterpane may be in the range of about 1% to 90% of the alkyl-adamantane fuel.

Sesquiterpenes are isolated from a renewable source. Sesquiterpenes can be generated by a biosynthetic process that utilizes sugar, biomass sugars, $CO_2$, or CO as a carbon source. Synthetic sesquiterpenes can be used and prepared directly from isoprene or from a reaction between terpenes and isoprene. Alternatively, sesquiterpenes can be extracted from plants using processes that include steam distillation and solvent extraction. Sesquiterpenes can be acyclic. Sesquiterpenes can be mono-cyclic and/or polycyclic hydrocarbons. Cyclic sesquiterpenes can be generated from acyclic sesquiterpenes.

Higher terpenes including diterpenes and triterpenes, can be thermally cracked to form sesquiterpenes. Examples of bio-derived sesquiterpenes that are feedstocks embodied in the invention are, but not limited to, farnesene, cadinene, selinene, humulene, copaene, clovene, alpha-neoclovene, longifolene, zizaene, thujopsene, other tricyclic sesquiterpenes, caryophyllene, isomerized caryophyllene mixtures, other bicyclic sesquiterpenes, monocyclic sesquiterpenes including bisabolene, and acyclic sesquiterpenes including farnesene. Bio-derived cyclopentadiene dimers and higher oligomers of bio-derived cyclopentadienes are also disclosed which includes alkylated versions (i.e. tetrahydrodimethyldicyclopentadiene) which we have shown can be generated from linalool, myrcene, and some sesquiterpenes.

The following are publications related to topics of the invention. The basic properties of petroleum-derived diamondoid-type fuels are described in: Chung, H. S.; Chen, C. S. H.; Kremer, R. A.; Boulton, J. R.; Burdette, G. W. Energy Fuels 1999, 13, 641-649. A recent paper has described the conversion of functionalized, hydrogenated cyclopentadienes to diamondoid fuels with ionic liquids: Ma, T.; Feng, R.; Zou, J-J.; Zhang, X.; Wang, Li Industrial and Engineering Chemistry Research 2013, 52, 2486-2492.

Isoprenoid feedstocks, including sesquiterpenes, are hydrogenated to generate saturated hydrocarbons. The hydrogenations can be conducted with either homogenous or heterogeneous catalysts under a hydrogen atmosphere. Hydrogenation catalysts based on nickel, palladium, platinum, ruthenium, and copper are suitable for the reduction. This can typically be conducted without a solvent. Hydrogenations may be conducted with or without a solvent. In some embodiments, addition of a polar solvent increases the reaction rate and allows for the use of milder conditions.

The saturated hydrocarbons are isomerized with acidic catalysts, including a strong Lewis acid or Bronsted acid. Examples of suitable Lewis acid catalysts include $AlCl_3$ and ionic liquids derived from or including $AlCl_3$. Heterogenous Lewis acid catalysts, mesoporous aluminosilicates (e.g. AlMCM-41), and amorphous aluminosilicates, can also be used. Lewis acidic ionic liquids and fluorinated sulfonic acids (heterogeneous and homogenous) are also suitable acidic catalysts for the isomerization.

When heterogeneous catalysts are used in a liquid-phase reaction, the hydrocarbon mixture may be separated by filtration, centrifugation, decantation and/or purified by distillation. In the case of homogenous catalysis, the catalyst may be quenched and the hydrocarbon may be separated by extraction and/or purified by distillation.

Purified alkyl-adamantane fuels may be used directly as high-density fuels or formulated with various conventional or renewable fuels to generate full-performance jet and diesel fuels.

There is a general method for converting an isoprenoid and/or functionalized isoprenoid feedstock to an alkyl-adamantane fuel. A first mixture is produced by hydrogenating the feedstock from about 1 to 48 hours with hydrogen gas at pressures ranging from about 1 atm to about 50 atm using a hydrogenation catalyst at temperatures ranging from about 10° to 200° C. An optional polar solvent may be used in the hydrogenation reactor or hydrogenation reaction zone. The first mixture may optionally be distilled to isolate hydrogenated fuel products, including a sesquiterpane. The first mixture is isomerized producing a second mixture. The isomerizing is carried out from about 0.3 to 48 hours using an acidic catalyst at pressures ranging from about 1 atm to about 10 atm at temperatures ranging from about 15° C. to 350° C. The isomerized second mixture is distilled to produce an alkyl-adamantane fuel, which is a mixture of alkyl-adamantanes and isomerized sesquiterpanes, or the second mixture is distilled to produce specific aklyadamantanes and/or specific isomerized sesquiterpanes.

Lewis acids, including acidic ionic liquids, are used to isomerize hydrogenated polycyclic hydrocarbons, including endotetrahydrodicyclopentadiene (endo-THDCPD) to exo-THDCPD, which is the major component of the synthetic fuel called JP-10. Furthermore, both endo- and exo-THDCPD can be converted to adamantane, the simplest diamondoid, via skeletal rearrangement (isomerization) using aluminum trichloride ($AlCl_3$) as the Lewis acid. The molar fraction of $AlCl_3$ in the ionic liquid determines the acidity of the solvent. Increasing the temperature of the reaction increases the reaction rate and can affect the percent conversion, selectivity, and ratios of various products obtained. A reasonable temperature range for the reaction is from 30° to 120° C. The fact that ionic liquids phase separate from nonpolar hydrocarbons make ionic-liquid-based methods suitable for continuous flow reaction systems.

A continuous-flow process for producing alkyl-adamantane fuel uses an isoprenoid and/or substituted isoprenoid feedstock, which may include sesquiterpenes. The feedstock is hydrogenated with hydrogen gas using a heterogeneous hydrogenation catalyst to produce first product stream, which is then isomerized using a heterogeneous acidic catalyst to produce a second product stream. The second product stream is distilled to produce an alkyl-adamantane fuel. The catalysts of the continuous-flow method are supported on fixed beds located in the respective zones. An optional polar solvent may be used, and is fed into the hydrogenating and isomerizing zone. The first product stream is produced by hydrogenating the feedstock having a residence time in the hydrogenation zone from about 0.5 to 48 hours with hydrogen gas at pressures ranging from about 1 atm to about 50 atm at temperatures ranging from about 10° C. to 200° C. The first product stream enters the isomerizing zone. The residence time in the isomerizing zone is about 0.2 to 48 hours at pressures ranging from about 1 atm to about 10 atm and at temperatures ranging from about 15° C. to 350° C. The second product stream exiting the isomerizing zone is distilled to produce an alkyl-adamantane fuel. When an ionic liquid is used, since it is insoluble in the nonpolar hydrocarbon products formed, it may be isolated from the fuel products and recycled back to the isomerizing zone. Optionally, a solid-state crosslinked ionic liquid-like material may be attached to a fixed bed in the isomerizing zone.

Example 1 n-Butyl-1-adamantaneketone 20 g of 1-adamantane carboxylic acid was dissolved in 250 mL THF and then cooled to −20° C. and while cold 93 mL 2.5 M n-BuLi (2.1 equiv) was added slowly dropwise over 1 h. Solids precipitated during this time and then the mixture was stirred at rt overnight. A standard workup generated 20.8 g crude oil. The product was further purified by distillation under reduced pressure. $^1$H ($CDCl_3$): 2.44 (t, J=7.1 Hz, 2H), 2.04 (m, 3H), 1.9-1.63 (m, 12H), 1.59-1.43 (m, 2H), 1.36-1.21 (m, 2H), 0.90 (t, J=7.7 Hz, 3H); 13C (CDCl3): 215.84, 46.45, 38.39, 36.78, 35.76, 28.16, 25.98, 22.62, 14.10. Analysis calcd for $C_{15}H_{24}O$: C, 81.76; H, 10.98. Found: C, 81.71; H, 11.00.

1-Pentyladamantane 2.3 g of n-butyl-1-adamantane ketone, 5 g hydrazine hydrate, 20 mL of diethylene glycol, and 5.6 g KOH were heated to 220° C. for 1 h, brought down to 180° C. for 3 h and then left overnight at 130° C. After a standard workup, this procedure gave 2.43 g of crude product (92%). Reduced pressure distillation gave the compound as a colorless liquid. When the reaction was conducted at ten times the scale, a yield of 97% was obtained. The product doesn't freeze when stored at −30° C. $^1$H ($CDCl_3$): 1.93 (m, 3H), 1.79-1.52 (m, 6H), 1.49-1.43 (m, 6H), 1.37-1.17 (m, 6H), 1.07-0.97 (m, 2H), 0.89 (t, J=7.2 Hz, 3H); 13C (CDCl3): 45.03, 42.82, 37.60, 33.17, 32.48, 29.08, 22.98, 22.29, 14.36. Analysis calcd for $C_{15}H_{26}$: C, 87.3; H, 12.7. Found: C, 87.14; H, 12.75.

Example 2

1-Pentyl adamantane, as an example of an alkyl-adamantane fuel, an embodiment of the invention, has a density of 0.946 g/mL, and a net heat of combustion (NHOC), measured by bomb calorimetry, of 145,997 btu/gal (relative standard deviation of 1.3%).

Example 3

Typical hydrogenation conditions for sesquiterpenes. Hydrogenation of sesquiterpenes including β-caryophyllene, valencene, and premnaspirodiene was conducted in a Parr shaker without the addition of solvent at room temperature and with an overpressure of 40-50 psi of hydrogen. Either 1 g of 10% Pd/C or 0.1 g of $PtO_2$ was used for every 100 g of sesquiterpene. The bomb was shaken until uptake of hydrogen ceased. The hydrogenation of valencene and premnaspirodiene was complete within two hours, while caryophyllene typically required up to 48 hours to fully react. After hydrogenation was complete, the black reaction mixtures were then filtered through a celite pad. Valencane, premnaspirodiane, and caryophyllane were used directly without further purification or were vacuum distilled (85-110° C., 1 Torr) through a 10 in Vigreux column to isolate the hydrogenated sesquiterpenes as colorless oils.

Example 4

Hydrogenation of Longifolane: 100 mL of longifolene, 30 mL of glacial acetic acid, and 0.1 g of PtO2 were added to a glass bomb. The bomb was placed under 45 psi hydrogen and shaken at room temperature for two h. The acetic acid was removed in a separatory funnel and the longifolane was washed with water (2×20 mL) and a 5% sodium carbonate solution. The longifolane was then purified by vacuum distillation.

Example 5

Hydrogenated sesquiterpanes are combined with an acid catalyst. The catalyst loading, reaction time, and temperature are dependent on the catalyst type. Some general reaction conditions are listed in Table 3. All reactions are conducted under an inert atmosphere and products were purified by either physical separation (heterogeneous catalysts) or quenching/extraction (homogenous catalysts) followed by isolation of either diamondoids or diamondoid/isomerized sesquiterpane mixtures by fractional distillation.

Prophetic examples are for illustration purposes only and not to be used to limit any of the embodiments. Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Embodiments of the invention generally relate to methods for synthesizing first alkyl-adamantane fuel including, providing a first isoprenoid and/or functionalized isoprenoid feedstock, producing first mixture by hydrogenating the first feedstock with hydrogen gas using at least one first hydrogenation catalyst, producing a second mixture by isomerizing the first mixture from about 0.3 hours to about 48 hours using a first acidic catalyst, and distilling the second mixture to produce the first alkyl-adamantane fuel. Another aspect of the invention generally relates to continuous-flow methods for synthesizing second alkyl-adamantane fuel including, providing second isoprenoid and/or functionalized isoprenoid feedstock, hydrogenating the second feedstock with hydrogen gas using second hydrogenation catalyst to produce first product stream, isomerizing the first product stream using second acidic catalyst to produce second product stream, and distilling the second product stream to produce the second alkyl-adamantane fuel.

In embodiments, in producing the first mixture the hydrogenation catalyst further includes at least one transition-metal selected from the group consisting of, but not limited to, nickel, palladium, platinum, ruthenium, and copper. In embodiments, in producing the first mixture, the hydrogenating further includes adding at least one polar solvent selected from the group consisting of, but not limited to, ethyl acetate, other organic ester, acetic acid, other organic acid, methanol, ethanol, butanol, THF, dioxane, and other alcohols and alcohols. In embodiments, the producing the first mixture further includes distilling the first mixture to produce at least one sesquiterpane. In embodiments, the homogeneous acidic catalyst is selected from the group consisting of, but not limited to, $AlCl_3$, $FeCl_3$, $TiCl_4$, $ZnCl_2$, $SbF_5$, $BF_3$, Lewis acids based on Ti, V, Cr, Mn, Fe, Co, Ni, Cu, Zn, Al, B, Sn, Sb in various oxidation states, and other homogeneous Lewis-acid compounds.

In embodiments, the producing the second mixture by isomerizing further includes adding at least one ionic liquid selected from the group consisting of, but not limited to, pyridinium ionic liquid, imidazolium ionic liquid, acidic ionic liquid, acidic chloroaluminate ionic liquid, clay-supported chloroaluminate ionic liquid, [1-butyl-3-methylimidazolium][bis(trifluoromethylsulfonyl imide)], [1-butyl-3-methylimidazolium][tricyanomethanide], [tri(butyl)(tridecyl)phosphoniumlibis(trifluoro methylsulfonyl imide)], triethylammonium chloroaluminate, [1-butyl-3-methylpyridinium] chloroaluminate, and [1-butyl-3-methylimidazolium] chloroaluminate. In embodiments, the acidic catalyst is a heterogeneous Lewis-acid selected from at least one of the group consisting of, but not limited to, $AlCl_3$, $FeCl_3$, $TiCl_4$, $ZnCl_2$, $SbF_5$, $BF_3$, Lewis acids based on Ti, V, Cr, Mn, Fe, Co, Ni, Cu, Zn, Al, B, Sn, Sb in various oxidation states, and other Lewis-acid compound, and where the heterogeneous acidic catalyst is supported on at least one solid material selected from the group consisting of, but not limited to, zeolite, aluminosilicate, alumina, zirconia, titania, silica, and clay, other acidic metal oxide, cross-linked sulfonated polystyrene, other macroreticular resin, other polymer, crosslinked ionic liquid, crosslinked poly(ionic liquid), and crosslinked ionic liquid gel.

In embodiments, the producing the first mixture by hydrogenating the first feedstock is from about 1 hour to 48 hours with hydrogen gas at pressures ranging from about 1 atm to about 50 atm using the first hydrogenation catalyst at temperatures ranging from about 10° C. to 200° C. and where the producing the second mixture by isomerizing the first mixture is from about 0.3 hour to about 48 hours using the first acidic catalyst at pressures ranging from about 1 atm to about 10 atm at temperatures ranging from about 15° C. to about 350° C. In embodiments, the first alkyl-adamantane fuel produced by the methods herein are included in a blended fuel including, but not limited to, Jet A, JP-10, JP-5, F-76, butene oligomer fuels, and hexene oligomer fuels. In embodiments, the hydrogenating the second feedstock with the second hydrogenation catalyst is a heterogeneous second hydrogenation catalyst supported on a fixed bed.

In embodiments, the hydrogenating further includes adding at least one polar solvent selected from the group consisting of, but not limited to, ethyl acetate, other organic ester, acetic acid, other organic acid, methanol, ethanol, butanol, and other alcohols. In embodiments, the isomerizing the first product stream of the second acidic catalyst is a heterogeneous second Lewis acid supported on a fixed bed. In embodiments, the first alkyl-adamantane fuel is produced by the methods herein is a blended fuel including Jet A, JP-10, JP-5, F-76, butene oligomers, and hexene oligomers. In other embodiments, the second alkyl-adamantane fuel being 1-pentyl adamantane is produced by the methods herein are a blended fuel including Jet A, JP-10, JP-5, F-76, biobutene, and biohexene.

In embodiments, the blended fuel has a density of at least 0.90 g/mL and a NHOC of at least 135,000 Btu/gal. In embodiments, the fuel has a cetane number ranging from about 30 to about 42. In embodiments, the blended fuel has a cetane number ranging from about 42 to about 50 and has from about 1% to about 70% of the alkyl-adamantane fuel.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A hydrogenated cedarwood oil produced by the methods, comprising:
   hydrogenating cedarwood oil in the presence of at least one hydrogenation catalyst to generate hydrogenated cedarwood oil;
   removing said hydrogenation catalyst from said hydrogenated cedarwood oil;
purifying said hydrogenated cedarwood oil to produce first high density fuels.

* * * * *